United States Patent
Fisher

(12) 
(10) Patent No.: US 9,345,473 B2
(45) Date of Patent: May 24, 2016

(54) IMPLANTABLE SLING SYSTEMS AND METHODS

(75) Inventor: Brian G. Fisher, Minneapolis, MN (US)

(73) Assignee: Astora Women's Health, LLC, Eden Prairie, MN (US)

(*) Notice: Subject to any disclaimer, the term of this patent is extended or adjusted under 35 U.S.C. 154(b) by 206 days.

(21) Appl. No.: 13/520,125

(22) PCT Filed: Dec. 30, 2010

(86) PCT No.: PCT/US2010/062546
§ 371 (c)(1),
(2), (4) Date: Sep. 13, 2012

(87) PCT Pub. No.: WO2011/082330
PCT Pub. Date: Jul. 7, 2011

(65) Prior Publication Data
US 2013/0006048 A1   Jan. 3, 2013

Related U.S. Application Data

(60) Provisional application No. 61/291,210, filed on Dec. 30, 2009, provisional application No. 61/291,372, filed on Dec. 31, 2009, provisional application No. 61/291,363, filed on Dec. 31, 2009.

(51) Int. Cl.
*A61F 2/00* (2006.01)
*A61B 17/06* (2006.01)
*A61B 17/00* (2006.01)

(52) U.S. Cl.
CPC . *A61B 17/06109* (2013.01); *A61B 2017/00805* (2013.01); *A61B 2017/06042* (2013.01); *A61F 2/0045* (2013.01)

(58) Field of Classification Search
CPC .................. A61B 17/0401; A61B 2017/0409; A61B 17/0487; A61B 2017/06176; A61B 2017/045; A61B 2017/00805; A61F 2/0045; A61F 2220/0016

USPC ..................... 600/37; 128/897–899
See application file for complete search history.

(56) References Cited

U.S. PATENT DOCUMENTS

| | | | |
|---|---|---|---|
| 2,738,790 A | 3/1956 | Todt et al. |
| 3,472,232 A | 10/1969 | Earl |
| 3,580,313 A | 5/1971 | McKnight |
| 3,763,860 A | 10/1973 | Clarke |
| 3,858,783 A | 1/1975 | Kapitanov et al. |
| 3,995,619 A | 12/1976 | Glatzer |
| 4,172,458 A | 10/1979 | Pereyra |
| 4,235,238 A | 11/1980 | Ogiu et al. |

(Continued)

FOREIGN PATENT DOCUMENTS

| | | |
|---|---|---|
| AU | 2002241673 AU | 11/2005 |
| CA | 2404459 | 8/2005 |

(Continued)

OTHER PUBLICATIONS

"We're staying ahead of the curve" Introducing the IVS Tunneller Device for Tension Free Procedures, Tyco Healthcare, 3 pages (2002).

(Continued)

*Primary Examiner* — Charles A Marmor, II
*Assistant Examiner* — Joshua D Lannu
(74) *Attorney, Agent, or Firm* — Skaar Ulbrich Macari, P.A.

(57) ABSTRACT

Various embodiments of sling or implant systems are provided. The sling or implant systems can be employed to treat incontinence, prolapse, and like conditions. A needle delivery device can be included, wherein the delivery device includes a needle and a rotatable sheath. The rotatable sheath can rotate upon actuation relative to the needle to selectively deploy or disengage an implant anchor from the distal end of the needle.

20 Claims, 9 Drawing Sheets

(56) References Cited

U.S. PATENT DOCUMENTS

| | | |
|---|---|---|
| 4,441,497 A | 4/1984 | Paudler |
| 4,509,516 A | 4/1985 | Richmond |
| 4,548,202 A | 10/1985 | Duncan |
| 4,632,100 A | 12/1986 | Somers et al. |
| 4,873,976 A | 10/1989 | Schreiber |
| 4,932,962 A | 6/1990 | Yoon et al. |
| 4,938,760 A | 7/1990 | Burton et al. |
| 4,969,892 A | 11/1990 | Burton et al. |
| 4,979,956 A | 12/1990 | Silvestrini |
| 5,013,292 A | 5/1991 | Lemay |
| 5,013,316 A | 5/1991 | Goble et al. |
| 5,053,043 A | 10/1991 | Gottesman et al. |
| 5,085,661 A | 2/1992 | Moss |
| 5,112,344 A | 5/1992 | Petros |
| 5,141,520 A | 8/1992 | Goble et al. |
| 5,149,329 A | 9/1992 | Richardson |
| 5,167,665 A | 12/1992 | McKinney |
| 5,188,636 A | 2/1993 | Fedotov |
| 5,203,864 A | 4/1993 | Phillips |
| 5,209,756 A | 5/1993 | Seedhom et al. |
| 5,234,438 A | 8/1993 | Semrad |
| 5,256,133 A | 10/1993 | Spitz |
| 5,268,001 A | 12/1993 | Nicholson et al. |
| 5,269,783 A | 12/1993 | Sander |
| 5,281,237 A | 1/1994 | Gimpelson |
| 5,328,077 A | 7/1994 | Lou |
| 5,337,736 A | 8/1994 | Reddy |
| 5,354,292 A | 10/1994 | Braeuer et al. |
| 5,368,595 A | 11/1994 | Lewis |
| 5,370,650 A | 12/1994 | Tovey et al. |
| 5,370,662 A | 12/1994 | Stone et al. |
| 5,376,097 A | 12/1994 | Phillips |
| 5,383,904 A | 1/1995 | Totakura et al. |
| 5,403,328 A | 4/1995 | Shallman |
| 5,439,467 A | 8/1995 | Benderev et al. |
| 5,474,518 A | 12/1995 | Velazquez |
| 5,474,543 A | 12/1995 | McKay |
| 5,520,700 A | 5/1996 | Beyar et al. |
| 5,520,703 A | 5/1996 | Essig |
| 5,527,342 A | 6/1996 | Pietrzak et al. |
| 5,544,664 A | 8/1996 | Benderev et al. |
| 5,562,689 A | 10/1996 | Green et al. |
| 5,571,139 A | 11/1996 | Jenkins, Jr. |
| 5,582,188 A | 12/1996 | Benderev et al. |
| 5,584,860 A | 12/1996 | Goble et al. |
| 5,591,163 A | 1/1997 | Thompson |
| 5,591,206 A | 1/1997 | Moufarrege |
| 5,611,515 A | 3/1997 | Benderev et al. |
| 5,628,756 A | 5/1997 | Barker, Jr. et al. |
| 5,643,320 A | 7/1997 | Lower et al. |
| 5,647,836 A | 7/1997 | Blake et al. |
| 5,669,935 A | 9/1997 | Rosenman et al. |
| 5,674,247 A | 10/1997 | Sohn |
| 5,683,349 A | 11/1997 | Makower et al. |
| 5,690,655 A | 11/1997 | Hart et al. |
| 5,697,931 A | 12/1997 | Thompson |
| 5,709,708 A | 1/1998 | Thal |
| 5,725,529 A | 3/1998 | Nicholson et al. |
| 5,725,541 A | 3/1998 | Anspach, III et al. |
| 5,741,282 A | 4/1998 | Anspach, III et al. |
| 5,782,862 A | 7/1998 | Bonuttie |
| 5,842,478 A | 12/1998 | Benderev et al. |
| 5,873,891 A | 2/1999 | Sohn |
| 5,899,909 A | 5/1999 | Claren et al. |
| 5,904,692 A | 5/1999 | Steckel et al. |
| 5,922,026 A | 7/1999 | Chin |
| 5,925,047 A | 7/1999 | Errico et al. |
| 5,944,732 A | 8/1999 | Raulerson et al. |
| 5,954,057 A | 9/1999 | Li |
| 5,972,000 A | 10/1999 | Beyar et al. |
| 5,980,558 A | 11/1999 | Wiley |
| 5,984,927 A | 11/1999 | Wenstrom, Jr. |
| 5,988,171 A | 11/1999 | Sohn et al. |
| 5,997,554 A | 12/1999 | Thompson |
| 6,007,539 A | 12/1999 | Kirsch et al. |
| 6,019,768 A | 2/2000 | Wenstrom et al. |
| 6,027,523 A | 2/2000 | Schmieding |
| 6,030,393 A | 2/2000 | Corlew |
| 6,036,701 A | 3/2000 | Rosenman |
| 6,042,583 A | 3/2000 | Thompson et al. |
| 6,048,351 A | 4/2000 | Gordon et al. |
| 6,053,935 A | 4/2000 | Brenneman et al. |
| 6,056,688 A | 5/2000 | Benderev et al. |
| 6,099,538 A | 8/2000 | Moses |
| 6,099,551 A | 8/2000 | gabby |
| 6,099,552 A | 8/2000 | Adams |
| 6,127,597 A | 10/2000 | Beyar et al. |
| 6,168,611 B1 | 1/2001 | Risvi |
| 6,200,330 B1 | 3/2001 | Benderev et al. |
| 6,241,736 B1 | 6/2001 | Sater et al. |
| 6,245,082 B1 | 6/2001 | Gellman et al. |
| 6,264,676 B1 | 7/2001 | Gellman et al. |
| 6,273,852 B1 | 8/2001 | Lehe et al. |
| 6,319,272 B1 | 11/2001 | Brenneman |
| 6,322,492 B1 | 11/2001 | Kovac |
| 6,328,744 B1 | 12/2001 | Harari et al. |
| 6,334,446 B1 | 1/2002 | Beyar |
| 6,382,214 B1 | 5/2002 | Raz et al. |
| 6,387,041 B1 | 5/2002 | Harari et al. |
| 6,406,423 B1 | 6/2002 | Scetbon |
| 6,406,480 B1 | 6/2002 | Beyar et al. |
| 6,423,072 B1 | 7/2002 | Zappala |
| 6,423,080 B1 | 7/2002 | Gellman et al. |
| 6,440,154 B2 | 8/2002 | gellman et al. |
| 6,451,024 B1 | 9/2002 | Thompson et al. |
| 6,454,778 B2 | 9/2002 | Kortenbach |
| 6,475,139 B1 | 11/2002 | Miller |
| 6,478,727 B2 | 11/2002 | Scetbon |
| 6,491,703 B1 | 12/2002 | Ulmsten |
| 6,502,578 B2 | 1/2003 | Raz et al. |
| 6,506,190 B1 | 1/2003 | Walshe |
| 6,530,943 B1 | 3/2003 | Hoepffner et al. |
| 6,544,273 B1 | 4/2003 | Harari et al. |
| 6,555,017 B1 | 4/2003 | Rushford et al. |
| 6,582,443 B2 | 6/2003 | Cabak et al. |
| 6,592,515 B2 | 7/2003 | Thierfelder |
| 6,592,610 B2 | 7/2003 | Beyar |
| 6,596,001 B2 | 7/2003 | Stormby et al. |
| 6,599,235 B2 | 7/2003 | Kovac |
| 6,602,260 B2 | 8/2003 | Harari et al. |
| 6,612,977 B2 | 9/2003 | Staskin et al. |
| 6,635,058 B2 | 10/2003 | Beyar et al. |
| 6,638,210 B2 | 10/2003 | Berger |
| 6,641,525 B2 | 11/2003 | Rocheleau |
| 6,648,921 B2 | 11/2003 | Anderson et al. |
| 6,673,010 B2 | 1/2004 | Skiba et al. |
| 6,685,629 B2 | 2/2004 | Therin |
| 6,689,047 B2 | 2/2004 | Gellman et al. |
| 6,691,711 B2 | 2/2004 | Raz et al. |
| 6,730,110 B1 | 5/2004 | Harari et al. |
| 6,736,829 B1 | 5/2004 | Li et al. |
| 6,746,455 B2 | 6/2004 | Beyar et al. |
| 6,752,814 B2 | 6/2004 | Gellman et al. |
| 6,802,807 B2 | 10/2004 | Anderson |
| 6,884,212 B2 | 4/2005 | Thierfelder et al. |
| 6,908,425 B2 | 6/2005 | Luscombe |
| 6,908,473 B2 | 6/2005 | Skiba et al. |
| 6,911,002 B2 | 6/2005 | Fierro |
| 6,911,003 B2 | 6/2005 | Anderson et al. |
| 6,932,759 B2 | 8/2005 | Kammerer |
| 6,936,052 B2 | 8/2005 | Gellman et al. |
| 6,971,986 B2 | 12/2005 | Staskin et al. |
| 6,974,462 B2 | 12/2005 | Sater |
| 6,981,983 B1 | 1/2006 | Rosenblatt et al. |
| 6,991,597 B2 | 1/2006 | Gellman et al. |
| 7,014,607 B2 | 3/2006 | Gellman |
| 7,025,063 B2 | 4/2006 | Snitkin et al. |
| 7,025,772 B2 | 4/2006 | Gellman et al. |
| 7,037,255 B2 | 5/2006 | Inman |
| 7,048,682 B2 | 5/2006 | Neisz et al. |
| 7,056,333 B2 | 6/2006 | Walshe |
| 7,070,556 B2 | 7/2006 | Anderson |
| 7,083,637 B1 | 8/2006 | Tannhauser |
| 7,087,059 B2 | 8/2006 | Harari et al. |

(56) References Cited

U.S. PATENT DOCUMENTS

| | | |
|---|---|---|
| 7,112,171 B2 | 9/2006 | Rocheleau et al. |
| 7,121,997 B2 | 10/2006 | Kammerer et al. |
| 7,131,943 B2 | 11/2006 | Kammerer |
| 7,189,251 B2 | 3/2007 | Kay |
| 7,223,229 B2 | 5/2007 | Inman et al. |
| 7,226,407 B2 | 6/2007 | Kammerer |
| 7,226,408 B2 | 6/2007 | Harari et al. |
| 7,229,404 B2 | 6/2007 | Bouffier |
| 7,229,453 B2 | 6/2007 | Anderson |
| 7,235,043 B2 | 6/2007 | Gellman et al. |
| 7,261,723 B2 | 8/2007 | Smith et al. |
| 7,267,645 B2 | 9/2007 | Anderson et al. |
| 7,291,104 B2 | 11/2007 | Neisz et al. |
| 7,297,102 B2 | 11/2007 | Smith et al. |
| 7,303,525 B2 | 12/2007 | Watschke et al. |
| 7,326,213 B2 | 2/2008 | Benderev et al. |
| 7,347,812 B2 | 3/2008 | Mellier |
| 7,351,196 B2 | 4/2008 | Goldmann et al. |
| 7,351,197 B2 | 4/2008 | Montpetit et al. |
| 7,357,773 B2 | 4/2008 | Watschke et al. |
| 7,364,541 B2 | 4/2008 | Chu et al. |
| 7,371,245 B2 | 5/2008 | Evans et al. |
| 7,387,634 B2 | 6/2008 | Benderev |
| 7,393,320 B2 | 7/2008 | Montpetit et al. |
| 7,407,480 B2 | 8/2008 | Staskin et al. |
| 7,410,460 B2 | 8/2008 | Benderev |
| 7,413,540 B2 | 8/2008 | Gellman et al. |
| 7,422,557 B2 | 9/2008 | Arnal |
| 7,494,495 B2 | 2/2009 | Delorme et al. |
| 7,500,945 B2 | 3/2009 | Coxt et al. |
| 7,517,313 B2 | 4/2009 | Thierfelder et al. |
| 7,527,588 B2 | 5/2009 | Zaddem et al. |
| 7,527,633 B2 | 5/2009 | Rioux |
| 7,547,316 B2 | 6/2009 | Priewe et al. |
| 7,588,598 B2 | 9/2009 | Delorme et al. |
| 7,601,118 B2 | 10/2009 | Smith et al. |
| 7,614,999 B2 | 11/2009 | Gellman et al. |
| 7,621,865 B2 | 11/2009 | Gellman et al. |
| 7,637,860 B2 | 12/2009 | MacLean |
| 7,686,759 B2 | 3/2010 | Sater |
| 7,686,760 B2 | 3/2010 | Anderson et al. |
| 7,691,050 B2 | 4/2010 | Gellman et al. |
| 7,691,052 B2 | 4/2010 | Gellman et al. |
| 7,740,576 B2 | 6/2010 | Hodroff |
| 7,753,839 B2 | 7/2010 | Siegel et al. |
| 7,762,942 B2 | 7/2010 | Neisz et al. |
| 7,828,715 B2 | 11/2010 | Haverfield |
| 2001/0000533 A1 | 4/2001 | Kovac |
| 2001/0018549 A1 | 8/2001 | Scetbon |
| 2001/0027321 A1 | 10/2001 | Gellman et al. |
| 2001/0041895 A1 | 11/2001 | Beyar et al. |
| 2001/0049467 A1 | 12/2001 | Lehe et al. |
| 2001/0053916 A1 | 12/2001 | Rioux |
| 2002/0007222 A1 | 1/2002 | Desai |
| 2002/0028980 A1 | 3/2002 | Thierfelder et al. |
| 2002/0035369 A1 | 3/2002 | Beyar et al. |
| 2002/0038119 A1 | 3/2002 | Weber et al. |
| 2002/0038132 A1 | 3/2002 | Abrams |
| 2002/0050277 A1 | 5/2002 | Beyar |
| 2002/0055748 A1 | 5/2002 | Gellman et al. |
| 2002/0058959 A1 | 5/2002 | Gellman et al. |
| 2002/0068948 A1 | 6/2002 | Stormby et al. |
| 2002/0077526 A1 | 6/2002 | Kammerer et al. |
| 2002/0082619 A1 | 6/2002 | Cabak et al. |
| 2002/0091373 A1 | 7/2002 | Berger |
| 2002/0095064 A1 | 7/2002 | Beyar |
| 2002/0095163 A1 | 7/2002 | Beyer et al. |
| 2002/0095181 A1 | 7/2002 | Beyar |
| 2002/0107525 A1 | 8/2002 | harari et al. |
| 2002/0128681 A1 | 9/2002 | Broome et al. |
| 2002/0147382 A1 | 10/2002 | Neisz et al. |
| 2002/0151762 A1 | 10/2002 | Rocheleau et al. |
| 2002/0151909 A1 | 10/2002 | Gellman et al. |
| 2002/0156487 A1 | 10/2002 | Gellman et al. |
| 2002/0156488 A1 | 10/2002 | Gellman et al. |
| 2002/0161382 A1 | 10/2002 | Neisz et al. |
| 2002/0188169 A1 | 12/2002 | Kammerer et al. |
| 2003/0004395 A1 | 1/2003 | Therin |
| 2003/0009181 A1 | 1/2003 | Gellman et al. |
| 2003/0023136 A1 | 1/2003 | Raz |
| 2003/0023138 A1 | 1/2003 | Luscombe |
| 2003/0036676 A1 | 2/2003 | Scetbon |
| 2003/0045774 A1 | 3/2003 | Staskin et al. |
| 2003/0050530 A1 | 3/2003 | Neisz et al. |
| 2003/0065402 A1 | 4/2003 | Anderson et al. |
| 2003/0171644 A1 | 9/2003 | Anderson et al. |
| 2003/0176875 A1 | 9/2003 | Anderson |
| 2003/0191360 A1 | 10/2003 | Browning |
| 2003/0225424 A1 | 12/2003 | Benderev |
| 2004/0015057 A1 | 1/2004 | Rocheleau et al. |
| 2004/0039453 A1 | 2/2004 | Anderson et al. |
| 2004/0172063 A1* | 9/2004 | Li et al. .................. 606/232 |
| 2004/0193215 A1 | 9/2004 | Harari et al. |
| 2004/0225181 A1 | 11/2004 | Chu et al. |
| 2004/0267088 A1 | 12/2004 | Kammerer |
| 2005/0000523 A1 | 1/2005 | Beraud |
| 2005/0004426 A1 | 1/2005 | Raz et al. |
| 2005/0004576 A1 | 1/2005 | Benderev |
| 2005/0065395 A1 | 3/2005 | Mellier |
| 2005/0131391 A1 | 6/2005 | Chu et al. |
| 2005/0131393 A1 | 6/2005 | Chu et al. |
| 2005/0143618 A1* | 6/2005 | Anderson et al. .............. 600/29 |
| 2005/0199249 A1 | 9/2005 | Karram |
| 2005/0245787 A1 | 11/2005 | Cox et al. |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt et al. |
| 2005/0283246 A1 | 12/2005 | Cauthen, III et al. |
| 2006/0004364 A1 | 1/2006 | Green et al. |
| 2006/0058578 A1 | 3/2006 | Browning |
| 2006/0089524 A1 | 4/2006 | Chu |
| 2006/0089525 A1 | 4/2006 | Mamo et al. |
| 2006/0173524 A1* | 8/2006 | Salahieh et al. .............. 623/1.11 |
| 2006/0195007 A1 | 8/2006 | Anderson |
| 2006/0217589 A1 | 9/2006 | Wam et al. |
| 2006/0229493 A1 | 10/2006 | Weiser et al. |
| 2006/0229596 A1 | 10/2006 | Weiser et al. |
| 2006/0252980 A1 | 11/2006 | Arnal et al. |
| 2006/0260618 A1 | 11/2006 | Hodroff et al. |
| 2006/0271074 A1* | 11/2006 | Ewers et al. .................. 606/148 |
| 2006/0287571 A1 | 12/2006 | Gozzi |
| 2007/0015953 A1 | 1/2007 | MacLean |
| 2007/0078295 A1 | 4/2007 | landgrebe |
| 2007/0173864 A1 | 7/2007 | Chu |
| 2008/0039678 A1 | 2/2008 | Montpetit et al. |
| 2008/0132753 A1* | 6/2008 | Goddard ......................... 600/37 |
| 2008/0300607 A1 | 12/2008 | Meade et al. |
| 2009/0012353 A1 | 1/2009 | Beyer |
| 2009/0036903 A1 | 2/2009 | Ino et al. |
| 2009/0137864 A1 | 5/2009 | Cox et al. |
| 2009/0156891 A1 | 6/2009 | Heys et al. |
| 2009/0182190 A1 | 7/2009 | Dann |
| 2009/0221867 A1 | 9/2009 | Ogdahl et al. |
| 2009/0221868 A1 | 9/2009 | Evans |
| 2009/0287229 A1 | 11/2009 | Ogdahl et al. |
| 2010/0010631 A1 | 1/2010 | Otte et al. |
| 2010/0094079 A1 | 4/2010 | Inman |
| 2010/0105979 A1 | 4/2010 | Hamel et al. |
| 2010/0152528 A1 | 6/2010 | Chapmenan et al. |
| 2010/0168595 A1 | 7/2010 | Inman et al. |
| 2010/0261952 A1 | 10/2010 | Montpetit et al. |
| 2010/0261955 A1 | 10/2010 | O'Hern et al. |
| 2011/0082328 A1 | 4/2011 | Gozzi et al. |
| 2011/0160529 A1* | 6/2011 | Crawford ....................... 600/37 |

FOREIGN PATENT DOCUMENTS

| | | |
|---|---|---|
| DE | 2305815 | 2/1973 |
| DE | 4220283 C2 | 5/1994 |
| DE | 10211360 | 9/2003 |
| DE | 20016866 | 3/2007 |
| EP | 0650703 A1 | 6/1994 |
| EP | 0643945 A2 | 7/1994 |

(56) References Cited

FOREIGN PATENT DOCUMENTS

| | | |
|---|---|---|
| EP | 0632999 A1 | 1/1995 |
| EP | 0643945 A2 | 3/1995 |
| EP | 1093758 A1 | 4/2001 |
| EP | 1342450 B1 | 9/2003 |
| FR | 2852813 A1 | 1/2004 |
| FR | 285217 | 10/2004 |
| GB | 2268690 A | 1/1994 |
| GB | 2353220 A | 10/2000 |
| SU | 1225547 A1 | 4/1986 |
| SU | 1342486 A | 10/1987 |
| WO | WO9310715 A1 | 6/1993 |
| WO | WO9319678 A2 | 10/1993 |
| WO | WO9511631 A1 | 5/1995 |
| WO | WO9525469 A1 | 9/1995 |
| WO | WO9716121 A1 | 5/1997 |
| WO | WO9730638 A1 | 8/1997 |
| WO | WO9747244 A1 | 12/1997 |
| WO | WO9819606 A1 | 5/1998 |
| WO | WO9835606 A1 | 8/1998 |
| WO | WO9835616 A1 | 8/1998 |
| WO | WO9842261 A1 | 10/1998 |
| WO | WO9853746 A1 | 12/1998 |
| WO | WO9937216 A1 | 7/1999 |
| WO | WO9937217 A1 | 7/1999 |
| WO | WO9952450 A1 | 10/1999 |
| WO | WO9953844 A1 | 10/1999 |
| WO | WO9958074 A2 | 11/1999 |
| WO | WO9959477 A1 | 11/1999 |
| WO | WO0013601 A1 | 3/2000 |
| WO | WO0030556 A1 | 6/2000 |
| WO | WO0040158 A2 | 7/2000 |
| WO | WO0057796 A1 | 10/2000 |
| WO | WO0074594 A1 | 12/2000 |
| WO | WO0074613 A1 | 12/2000 |
| WO | WO0074633 A2 | 12/2000 |
| WO | WO0230293 A1 | 4/2002 |
| WO | WO0232284 A2 | 4/2002 |
| WO | WO0234124 A2 | 5/2002 |
| WO | WO0239890 A2 | 5/2002 |
| WO | WO02058563 A1 | 8/2002 |
| WO | WO02062237 A1 | 8/2002 |
| WO | WO02069781 | 9/2002 |
| WO | WO02071953 A2 | 9/2002 |
| WO | WO03013392 A2 | 2/2003 |
| WO | WO03017848 A1 | 3/2003 |
| WO | WO03034891 A2 | 5/2003 |
| WO | WO03034939 A1 | 5/2003 |
| WO | WO03047435 A1 | 6/2003 |
| WO | WO03068107 A1 | 8/2003 |
| WO | WO03075792 A1 | 9/2003 |
| WO | WO03086205 A2 | 10/2003 |
| WO | WO03092546 A2 | 11/2003 |
| WO | WO03096928 A1 | 11/2003 |
| WO | WO03096929 A1 | 11/2003 |
| WO | WO2004016196 A2 | 2/2004 |
| WO | WO2004034912 A1 | 4/2004 |
| WO | WO2005004727 A1 | 1/2005 |
| WO | WO2005046511 A2 | 5/2005 |
| WO | WO2005048850 A2 | 6/2005 |
| WO | WO2005079702 A1 | 9/2005 |
| WO | WO2005122954 A1 | 12/2005 |
| WO | WO2006007189 A1 | 1/2006 |
| WO | WO2006007190 A1 | 1/2006 |
| WO | WO2006031879 A1 | 3/2006 |
| WO | WO2006069078 | 6/2006 |
| WO | WO2006108145 A1 | 10/2006 |
| WO | WO2007002012 A1 | 1/2007 |
| WO | WO2007002071 A1 | 1/2007 |
| WO | WO2007014241 A1 | 2/2007 |
| WO | WO2007016083 A1 | 2/2007 |
| WO | WO2007016698 A1 | 2/2007 |
| WO | WO2007027592 A2 | 3/2007 |
| WO | WO2007059199 A2 | 5/2007 |
| WO | 2007097994 A2 | 8/2007 |
| WO | WO2007097994 | 8/2007 |
| WO | WO2007137226 A2 | 11/2007 |
| WO | WO2007146784 A2 | 12/2007 |
| WO | WO2007149348 A2 | 12/2007 |
| WO | 2008057261 A2 | 5/2008 |
| WO | WO2008057261 A2 | 5/2008 |
| WO | WO2008124056 A1 | 10/2008 |
| WO | WO2009005714 A2 | 1/2009 |
| WO | 2009017680 A2 | 2/2009 |
| WO | WO2009017680 A2 | 2/2009 |
| WO | WO 2009038781 A1 * | 3/2009 |

OTHER PUBLICATIONS

Advantage A/T™, Surgical Mesh Sling Kit, Boston Scientific, 6 pages (2002).
Benderev, Theodore V., MD, A Modified Percutaneous Outpatient Bladder Neck Suspension System, Journal of Urology, vol. 152, pp. 2316-2320 (Dec. 1994).
Benderev, Theodore V., MD, Anchor Fixation and Other Modifications of Endoscopic Bladder Neck Suspension, Urology, vol. 40, No. 5, pp. 409-418 (Nov. 1992).
Capio™ CL—Transvaginal Suture Capturing Device—Transvaginal Suture Fixation to Cooper's Ligament for Sling Procedures, Boston Scientific, Microvasive®, 8 pages, (2002).
Cook/Ob Gyn®, Urogynecology, Copyright Cook Urological Inc., pp. 1-36 (1996).
Dargent, D. et al., Insertion of a Suburethral Sling Through the Obturator Membrane in the Treatment of Female Urinary Incontinence, Gynecol Obstet Fertil, vol. 30, pp. 576-582 (2002).
Gynecare TVT Tension-Free Support for Incontinence, the tension-free solution to female Incontinence, Gynecare Worldwide, 6 pages, (2002).
IVS Tunneller—A Universal instrument for anterior and posterior intra-vaginal tape placement, Tyco Healthcare, 4 pages (Aug. 2002).
IVS Tunneller—ein universelles Instrument fur die Intra Vaginal Schlingenplastik, Tyco Healthcare, 4 pages (2001).
IVS Tunneller, Australian Medical Design Breakthrough for GSI, mixed incontinence and vault prolapse, AMA Medical Products, 4 pages (no date).
Karram, Mickey M. et al., Chapter 19 Surgical Treatment of Vaginal Vault Prolapse, Urogynecology and Reconstructive Pelvic Surgery, (Walters & Karram eds.) pp. 235-256 (Mosby 1999).
Kovac, S. Robert, et al, Pubic Bone Suburethral Stabilization Sling: A Long Term Cure for SUI?, Contemporary OB/GYN, 10 pages (Feb. 1998).
Mitek Brochure, Therapy of Urinary Stess Incontinence in Women Using Mitek GIII Anchors, by Valenzio C. Mascio, MD.
Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advaned Surgical Techniques, vol. 9, No. 1 p.
Readjustable REMEEX® system, Neomedic International, 8 pages (no date).
SABRE™ Bioabsorbable Sling, Generation Now, Mentor, 4 pages (May 2002).
SABRE™ Surgical Procedure, Mentor, 6 pages (Aug. 2002).
Sanz, Luis E. et al., Modification of Abdominal Sacrocolpopexy Using a Suture Anchor System, The Journal of Reproductive Medicine, vol. 48, n. 7, pp. 496-500 (Jul. 2003).
Ulmsten, U. et al., An Ambulatory Surgical Procedure Under Local Anesthesia for Treatment of Female Urinary Incontinence, International Urogynecology Journal, vol. 7, pp. 81-86 (May 1996).
Ulmsten, Ulf et al., A Three Year Follow Up of Tension Free Vaginal Tape for Surgical Treatment of Female Stress Urinary Incontinence, British Journal of Obstetrics and Gynaecology, vol. 106, pp. 345-350 (1999).
UroMed Access Instrument System for the Sub-urethral Sling Procedure Catalog No. 120235, Directions for Use, (3 pages).
Vesica® Percutaneous Bladder Neck Stabilization Kit, a New Approach to Bladder Neck Suspenison, Microvasive® Boston Scientific Corporation, 4 pages (1995).
Precision Twist, Low Profile design for Precise Anchor Placement, Boston Scientific Microvasive, 2001 2 pp.
Vesica Sling Kit, Microvasive Boston Scientific, 1997, 6pp.
Precision Tack, The Precise Approach to Transvaginal Sling Procedures, Boston Scientific, 1998, 4pp.

(56) References Cited

OTHER PUBLICATIONS

International Search Report and the Written Opinion rendered by the International Searching Authority on Mar. 7, 2011, 11 pages.

Office Action to the corresponding EP Patent Application No. 10841735.3 rendered by the European Patent Office on Dec. 5, 2014, 1 page.

Office Action to the corresponding EP Patent Application No. 10841735.3 rendered by the European Patent Office on Aug. 14, 2015, 4 pages.

Office Action (Patent Exam Report No. 1) to the corresponding AU Patent Application No. 2010339416 rendered by the Australian Patent Office on Mar. 28, 2013, 4 pages.

Extended European Search Report to the corresponding EP Patent Application No. 10841735.3 rendered by the European Patent Office on Nov. 18, 2014, 6 pages.

Office Action (Patent Exam Report No. 1) to the corresponding AU Patent Application No. 2013224689 rendered by the Australian Patent Office on Dec. 16, 2014, 2 pages.

\* cited by examiner

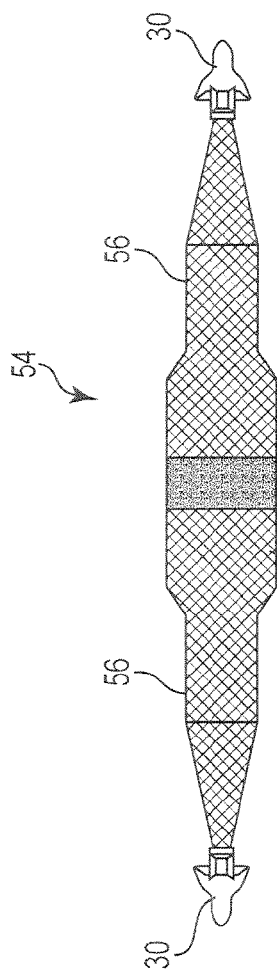
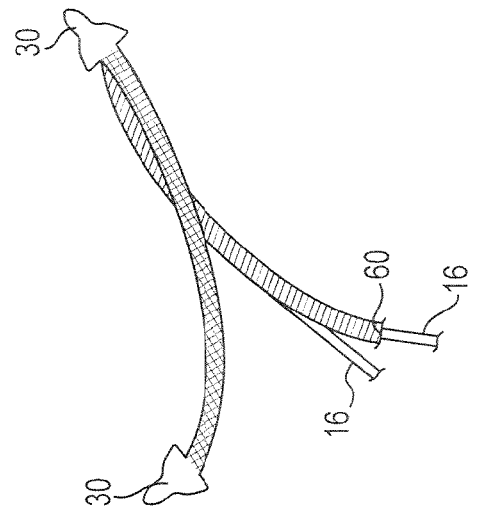
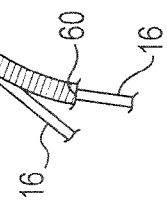

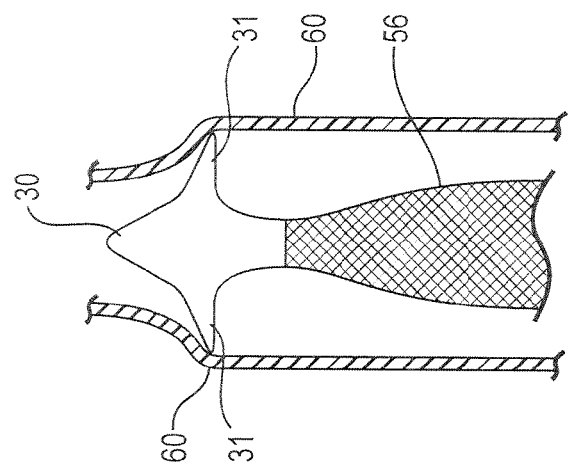
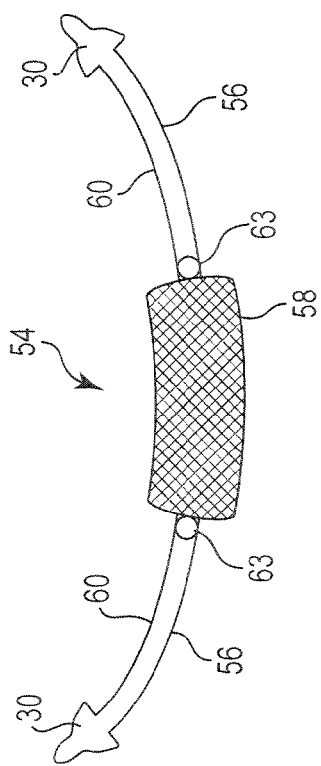

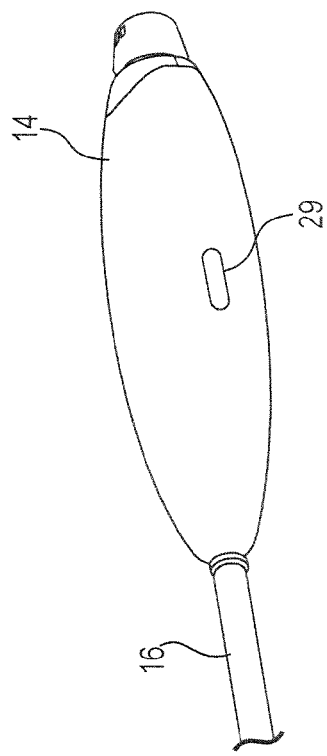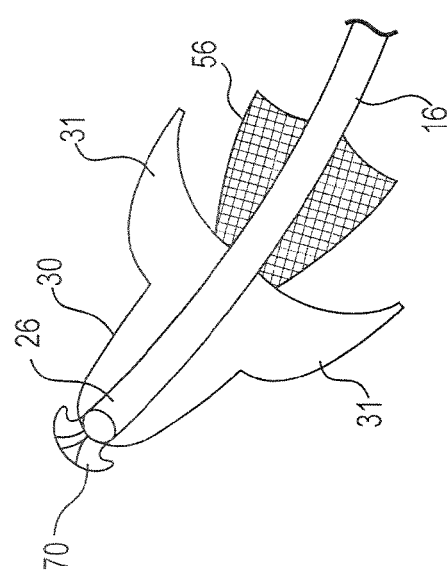
Fig. 19

IMPLANTABLE SLING SYSTEMS AND METHODS

PRIORITY

This application claims priority to and the benefit of U.S. Provisional Application Nos. 61/291,210, filed Dec. 30, 2009, 61/291,372, filed Dec. 31, 2009, and 61/291,363, filed Dec. 31, 2009; wherein each of the referenced applications are incorporated herein by reference in their entirety.

FIELD OF THE INVENTION

The present invention relates generally to surgical methods and apparatus and, more specifically, to surgically implantable mesh or sling devices and methods for using and deploying the same.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

There is a desire to obtain a minimally invasive yet highly effective implantable mesh that can be used to treat incontinence, and/or pelvic organ prolapse and other conditions.

SUMMARY OF THE INVENTION

The present invention describes pelvic mesh implants and methods for treating pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness.

Embodiments of the systems can include one or more needle delivery devices and an implant. The implants can be elongate sling devices, or pelvic prolapse implants. Each implant can generally include a support portion, one or more extension or arm portions, and one or more end anchors. One or more portions of the slings or implants can be constructed of a mesh material.

Various embodiments of the systems can include a needle delivery device having an actuation mechanism and rotatable sheath. The rotatable sheath can shroud or otherwise be provided along at least a portion of the curved or straight needle of the delivery device, and in operable communication with the actuation mechanism. Engagement or activation of the actuation mechanism rotates the sheath to selectively disengage or deploy the anchors of the implant from a distal tip of the needle device.

Certain embodiments of the implant and delivery device can include tube, sheath or like docking or re-docking features to facilitate selective engagement and deployment of the anchor and implant from the device. The anchors can be adapted to penetrate and engage in selected target tissue within the pelvis proximate, at, adjacent, or lateral the urethra, vagina, obturator foramen, endopelvic fascia, bladder, pelvic floor, elevator muscles, and the like.

Embodiments of the present invention may be incorporated into or provided with various commercial products marketed by American Medical Systems of Minnetonka, Minn., e.g., the MiniArc® or MiniArc® Precise Sling Systems.

BRIEF DESCRIPTION OF THE DRAWINGS

FIG. 7 is a top view of a mesh sling implant in accordance with embodiments of the present invention.

FIGS. 8-9 are schematic views of a sling implant, and tube docking/re-docking features or portions in accordance with embodiments of the present invention.

FIG. 10 is a top view of sling implant having a mesh support portion, and extension portions or arms in accordance with embodiments of the present invention.

FIG. 11 is a close-up partial schematic view of a tube or sheath extending substantially around a sling implant and anchor in accordance with embodiments of the present invention.

FIG. 19 is shows a needle delivery device and distal needle tip configuration in accordance with embodiments of the present invention.

DETAILED DESCRIPTION OF PREFERRED EMBODIMENTS

The present invention generally provides a sling or implant system 10 adapted for insertion to selectively deploy one or more implants or slings to treat various pelvic conditions, including incontinence (e.g., fecal or urinary), pelvic organ prolapse (e.g., rectal or vaginal), or other like conditions. The systems 10 of the present invention can include delivery devices, implants, docking/re-docking features and like configurations, features and devices to facilitate deployment and sling implantation.

The various systems, features and methods detailed herein are envisioned for use with or can incorporate devices, portions or methods of known pelvic implants, tissue or organ repair systems (e.g., for male and female), including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261 and WO 2007/097994, and U.S. Patent Publication Nos. 2010/0105979 2010/0261955, 2002/151762 and 2002/147382. Accordingly, the above-identified disclosures are fully incorporated herein by reference in their entirety.

Figure 1:
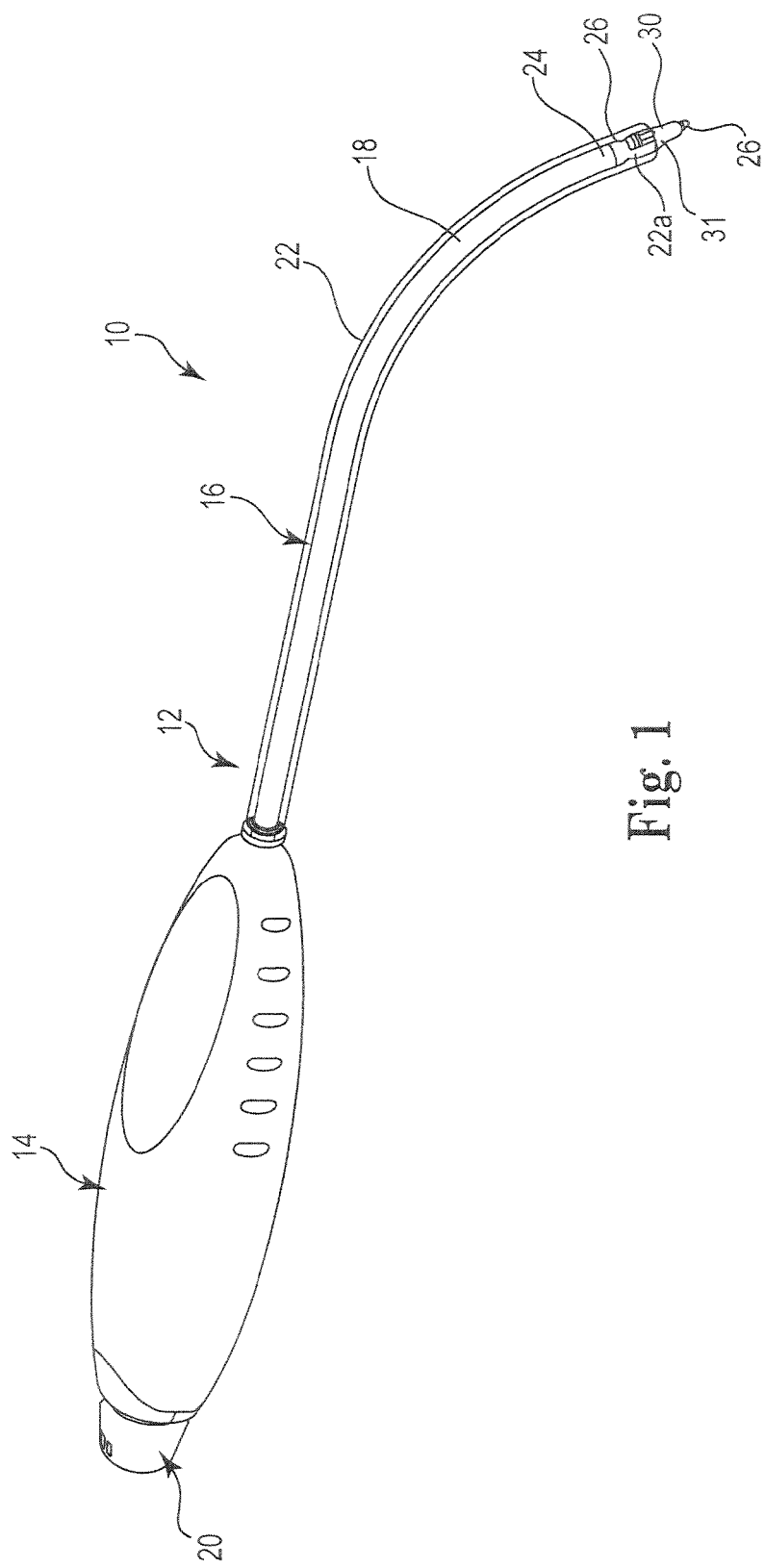
FIG. 1 is a perspective view of a needle delivery device with a rotatable sheath in accordance with embodiments of the present invention.
Figure 2:
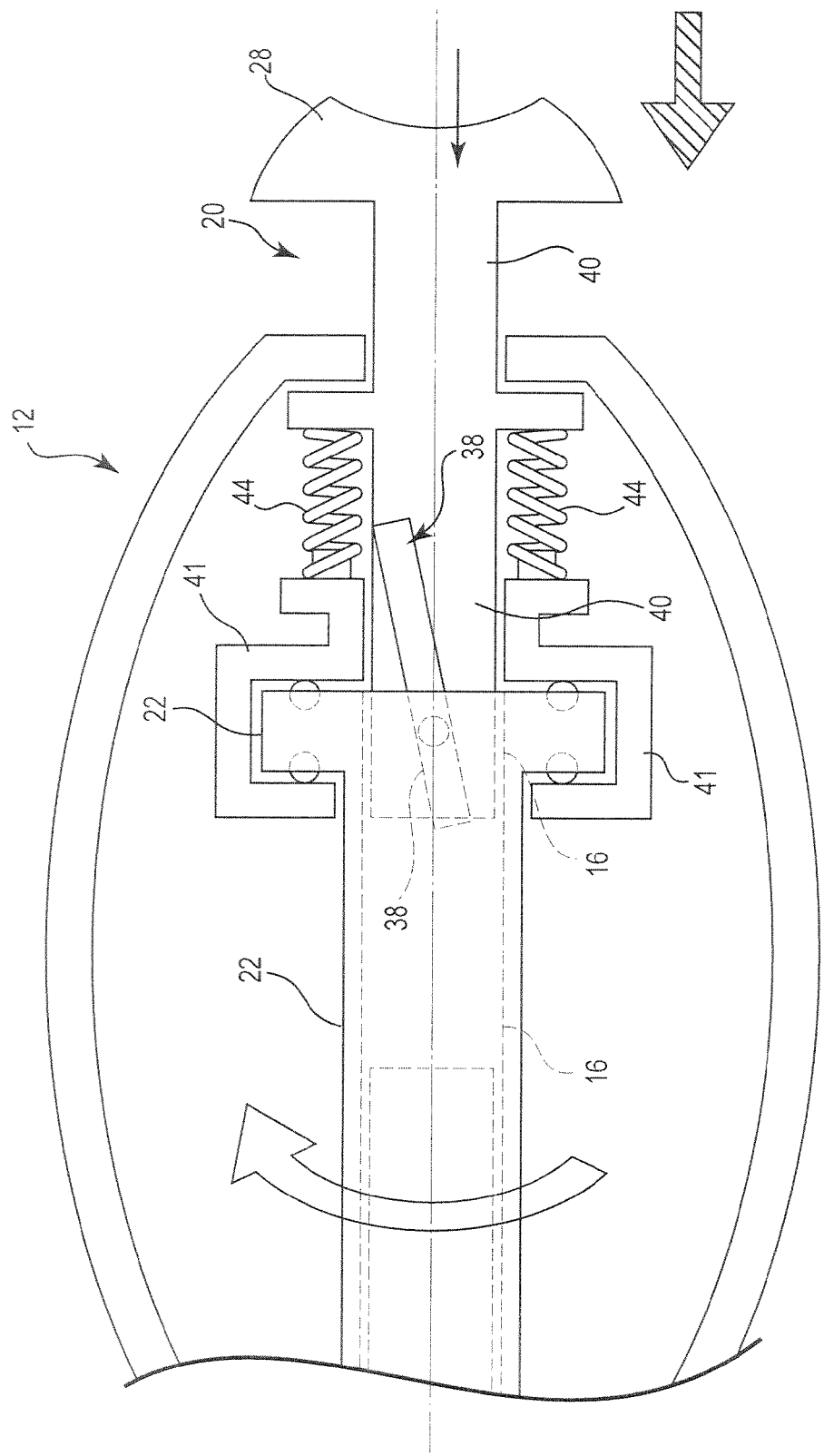
FIG. 2 is a schematic close-up cross-sectional view of a portion of a needle delivery device handle and actuation mechanism in accordance with embodiments of the present invention.
Figure 3:
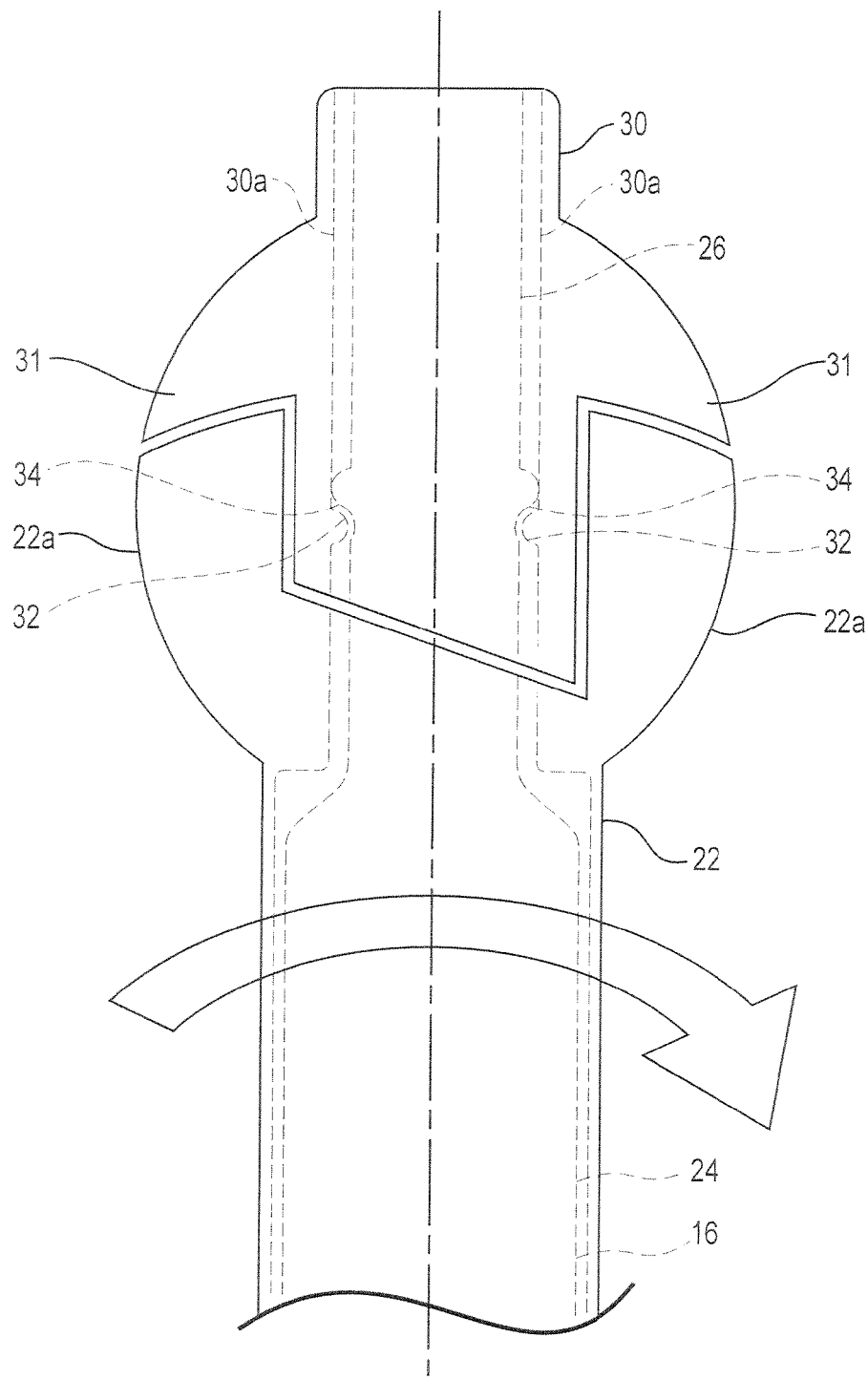
FIG. 3 is a schematic close-up cross-sectional view of a portion of a needle delivery device distal end, anchor and rotatable sheath in accordance with embodiments of the present invention.

Referring generally to FIGS. 1-3, embodiments of an implant delivery system 10 are shown. The implant delivery system 10 can include a delivery tool 12, having a handle 14 and a needle portion 16. The handle portion 14 can include an actuation mechanism 20. The needle portion 16 can include a needle 18, a rotatable sheath or tube 22 and a distal end portion 24. In various embodiments, the needle 18 can be hollow, solid, curved, straight, helical, or can take on a myriad of other like and compatible configurations. The sheath 22 generally shrouds a length of the needle portion 16. The distal end portion 24 can include an anchor retention and deployment tip 26.

The actuation mechanism 20 can include a button, slider or like actuator 28 in operable communication with at least the sheath 22 such that engagement or activation of the button 28 will cause the sheath 22 to rotate about the needle 16. FIGS. 2-3 show an embodiment of the handle 14 and distal end portion 24 of the needle 16, wherein pressing on or actuation of the button 28 rotates the sheath 22 to correspondingly deploy, push or release a tissue anchor 30 from the needle portion 16. For retention (e.g., snap engagement) of the anchor 30 on the distal tip 26 of the needle portion, embodiments of the anchor 30 can include small protrusions, ribs, ridges, indents or other features 32 within the lumen 30a of the anchor 30. Corresponding, reversed or mirrored features 34 can be included at the end of the engaged distal tip 26. Snap engagement of the anchor 30 to the tip 26 is provided with the features 32, 34 such that the anchor 30 is retained on the needle portion 16 until the time of selective disengagement during final deployment within the patient's soft tissue. This configuration further allows for audible and tactile feedback of engagement of the anchor 30 to the tip 26. The level of force needed to snap engage anchor 30 and needle 16 can vary greatly, depending on the materials used for the components, and the construct of the features 32, 34. As depicted in FIG. 3, the anchor 30 is initially keyed to the needle body (e.g., tip 26) such that the anchor 30 cannot rotate, but can slide longitudinally. The sheath 22 can include a barb guard 22a at the end proximate or at the distal end 24. The barb guard 22a and anchor 30 interface can be angled, straight, undulating, or take on various other configurations to facilitate the described snap engagement or retention. The anchor 30 can include one or more tines 31 adapted to mateably or abuttably engage corresponding surfaces or extensions in the barb guard 22a.

The actuation mechanism 20 within the handle 14 can include a cam or follower mechanism 38 causing the sheath 22 to rotate around the needle shaft, such that the anchor 30 is caused to move longitudinally in a distal direction off of the end of the tip 26. This longitudinal distal force on the anchor 30 by the cam mechanism 38 can be sufficient to overcome the retention force of the anchor 30 with the needle in accordance with the anchor retention features described herein. As such, once the retention features are disengaged, the anchor 30 slides freely from its distal position on the needle tip 26 and is thereby deployed.

Referring to FIG. 2, actuation mechanism 20 within the handle can include a barrel 40 adapted for longitudinal displacement within the handle 14 housing. In general, the barrel 40 is restricted from rotational movement. A proximal end of the sheath 22 is constrained within a housing boundary 41 such that it can rotate, but does not move longitudinally. As such, longitudinal movement of the button 28 and barrel 40 causes the sheath 22 to rotate. For example, the sheath 22 can include one or more cam mechanisms or features 38, generally opposed by 180 degrees. The barrel 40 can further include one or more cams, generally opposed by 180 degrees. Compression springs 44 are included and provide a resetting feature.

Various advantages of the embodiments depicted in FIGS. 1-3 include, a self-resetting handle mechanism 20, a convenient handle actuator 28, anchor tines 31 retained until deployment, minimization of tissue disruption by anchor tines 31 during anchor deployment, repeatable and secure engagement and disengagement of the anchor 30 and the needle 16, as well as tactile and audible feedback with the anchor 30 engagement. The various features and mechanisms, or portions thereof, can be constructed of known and compatible metals and polymers.

Figure 4:
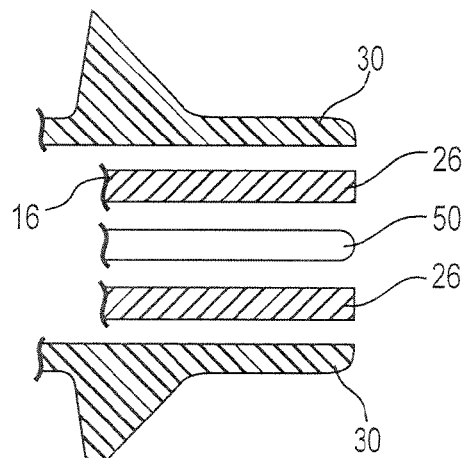
FIGS. 4-6 are schematic cross-sectional partial views of an anchor, distal needle tip, and retention feature in accordance with embodiments of the present invention.
Figure 5:
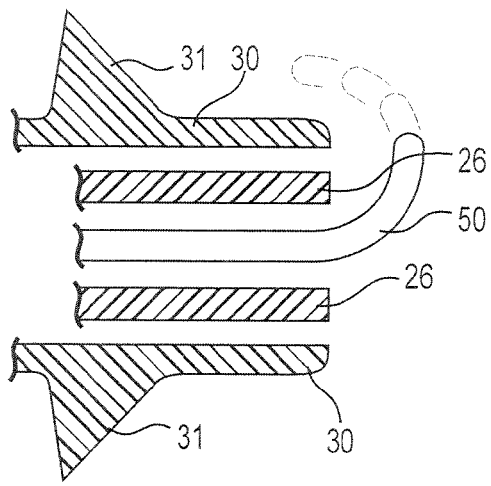
Figure 6:
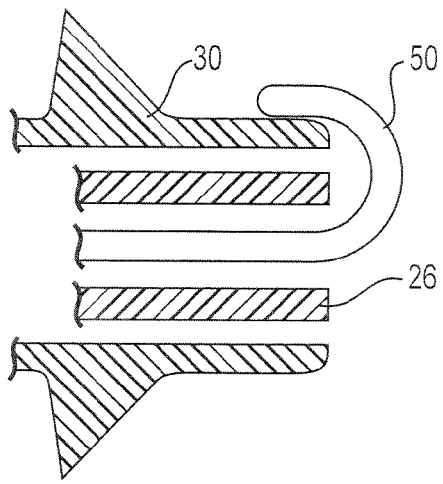
Figure 13:
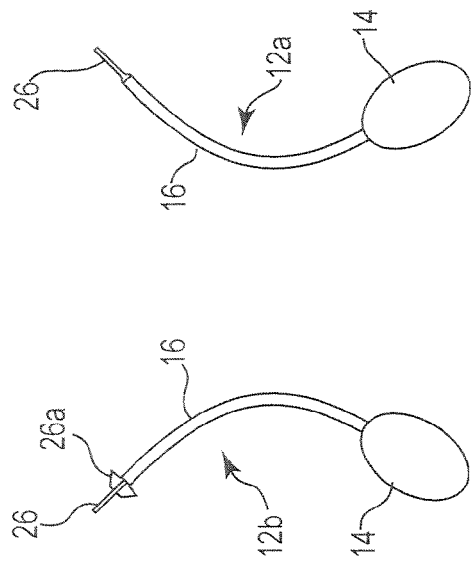
FIGS. 12-15 show a sling implant and delivery system having multiple needle delivery devices in accordance with embodiments of the present invention.
Figure 15:
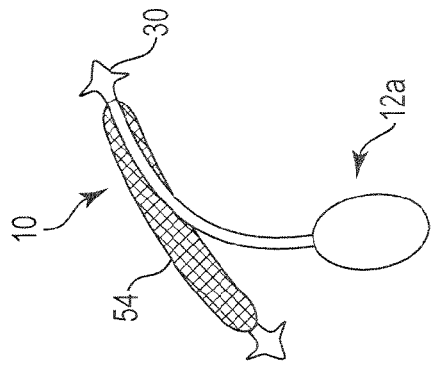
Figure 12:
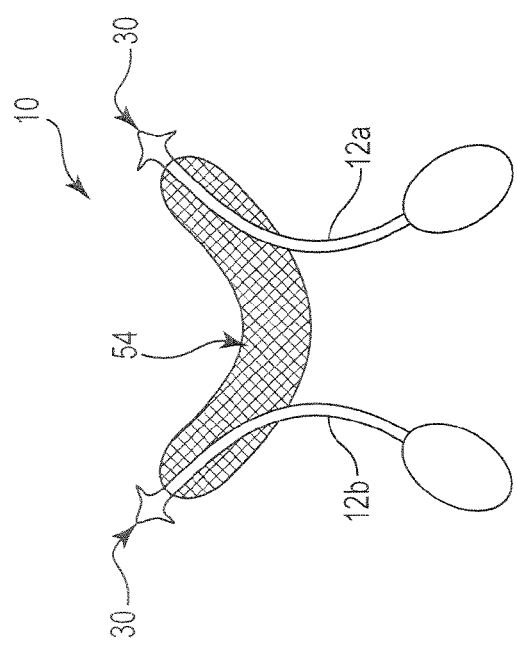
Figure 14:
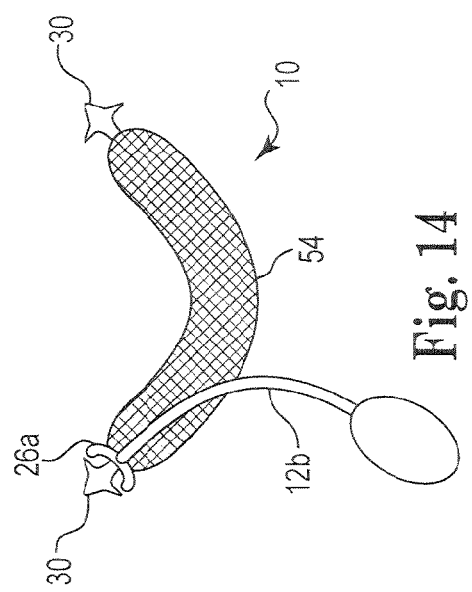

Referring generally to FIGS. 4-6, selective engagement and retention of the anchor 30 to the needle tip 26 for various embodiments are shown. Such embodiments can include a selectively extendable and retractable fixation member 50. The fixation member 50 is adapted to traverse, generally longitudinally, within or along the lumen of the hollow needle body 16. The fixation member 50 can be a shape memory wire or member, such as a Nitinol or other like wire materials, adapted to move in and out of the distal tip portion 26 of the needle 16 upon actuation by an end user (e.g., button or actuator in the handle 14). Various handle 14 and actuation members 28 can be included in operable communication with the member 50 to facilitate displacement of the member 50.

While traversing within the needle 16, or along an outer portion of the needle in alternative embodiments, the member 50 is retained in a generally longitudinal configuration or shape (FIG. 4). As a portion of the member 50 is deployed out of the distal tip 26 of the needle 16, at least a portion of the member 50 is generally free to resume its default shape, such as a curved or angled configuration. As such, the tip or end portion of the member 50 will tend to move or curve around the distal tip 26 to engage or otherwise retain the anchor 30 attached or provided at the distal tip 26 (FIG. 5). This will, in turn, secure the anchor 30 to the distal tip 26 such that the anchor 30 can be inserted, positioned and ultimately fixated within a target tissue site (FIG. 6).

Upon reaching the desired target tissue site, the anchor 30 can be released from the distal tip 26 of the needle 16. Namely, the user can retract or otherwise activate the member 50 such that the member 50 retreats or retracts back toward or into the needle tip 26. At this point, the needle 16 can be retracted, leaving the tissue anchor 30 in place or fixated to the target tissue site.

Referring generally to FIGS. 7-19, various embodiments of implantable sling or implant systems 54 are provided. In general, the implant 54 can be a mesh or patterned strut construct having extending portions 56 and a support portion 58. One or more anchors 30 can be included at the end portions of the extension portions 56. Various portions of the implants 54 can be constructed of polymer materials, such as a film or sheet material of polypropylene, polyethylene, fluoropolymers or like compatible materials.

Referring generally to FIGS. 8-19, various embodiments of the mesh or sling implant 54 are shown with various docking or re-docking features. Such re-docking features facilitate repositioning of the anchor 30 with the introducer needle 16, in or out of the patient's body. In one embodiment, a tube or sheath 60 is provided such that the introducer needle 16 is insertable within the tube 60. The tube 60 may encircle the needle 16, it may be integral with the sling or implant 54, or even made from the mesh or other portion of the implant 54. In other instances, the tube 60 can be a separate component, and may be semi-circular, v-shaped, or u-shaped rather than completely encircling the needle 16, to at least partially guide the needle 16 along the tube 60. The tube 60 can be removed with an axial tensile pull or with relative rotation (e.g., similar to a plastic bottle cap). As shown in FIG. 8, the tear away portion can include a thin tab 61 adapted to break the anchor 30 away from the needle 16 and/or tube 60 with a twisting motion.

The needle 16 can generally provide a counter force to the twist or rotation to ensure the anchor 30 position is not changed. Further, a barb guard can be included at a distal portion of the tube 60. The barb guard can provide a guard to prevent the tines 31 of the anchor 30 from engaging tissue until the moment of deployment, and can further serve to abut or provide a slight press fit with the anchor 30. The tube 60 provides a convenient, consistent and stable means of engagement or docking the needle 16 with the anchors 30 or sling 54.

The tube or sheath 60 can be torn away after positioning of the anchor 30 and deployment within target tissue. This can be done bilaterally for the two tubes 60, e.g., both extension portions 56 or end anchors 30. Perforations, slots, grooves, and like configurations can be included with the tube 60 to facilitate this tear away feature. The needle 16, or a portion thereof, can be inserted into an end of the hollow tube 60, or can be guided along an external surface or portion of the tube 60 (both shown in FIG. 9)

As detailed, the guide sheath or tube 60 can extend from the implant 54 to provide a channel or groove path for the needle to engage the anchors 30. The guide tube 60 can be constructed in a c-shaped, u-shaped, v-shaped or similar configuration to facilitate guidance of the needle. The tube 60 can be weakly attached (e.g., tear away bonds or welds) to the mesh implant 54 such that the tube 60 can be selectively torn away or otherwise removed from the implant.

The embodiment of FIG. 10 can include an implant 54 having the center mesh support portion 58, with lateral arms or extension portions 56 extending therefrom. The lateral arms 56 can be included with the tube 60 to again facilitate engagement and guidance of a needle 16 to the anchors 30. The lateral arms 56 can be constructed of wrapped mesh, hollow tube material, or take on a myriad of other configurations and material constructs. The arms 56 can further include one or more ports 63 adapted to facilitate entry and exit of the needle 16 or tip 26 for engagement and deployment of the anchor 30.

As shown in FIG. 11, various sheath or tube 60 embodiments can extend above or around at least a portion of the anchors 30. As such, the tube 60 can be longitudinally moved to slide away from the anchors 30 at deployment or implantation. The tube 60 can be perforated or scored to further facilitate removal. Again, the tube 60 can protect the barbs or tines 31 of the anchor 30 from engaging tissue until final implantation.

Referring to FIGS. 12-15, the sling or implant system 10 can include two needle delivery devices 12 rather than a single needle device. The needle device 12 can be adapted to engage and manipulate a corresponding anchor 30 of the implant 54. As such, deployment, manipulation, and tensioning can be applied to the implant 54 by one or both of the needle devices. In one embodiment, as shown in FIGS. 11-15, one of the needle devices 12a can include a barb guard 26a, with the other device 12b not having a barb guard. The needle device 12a can be used to anchor the sling on a second target tissue location, thus facilitating tensioning (advancing and retracting needle/anchor) without engaging the barbs 31 of the anchor 30 with the tissue until the desired tension is obtained.

In various embodiments, the anchors 30 can include pivotable, moveable, expandable or collapsible tines 31. In an initial insertion stage, the tines 31 lay generally flat or substantially angled toward the implant 54 or anchor 30 body to prevent engagement of the tines 31 with tissue. Upon deployment, the tines 31 can be forceably or automatically extended out to facilitate engagement with the target tissue location. Expansion and retraction of the tines 31 can be achieved by suture releases, or mechanical or manual means. The anchor 30 or tines 31 can be constructed of acceptable or known materials (e.g., shape memory) and constructs to facilitate such moveable or collapsible functionality.

Figure 16:
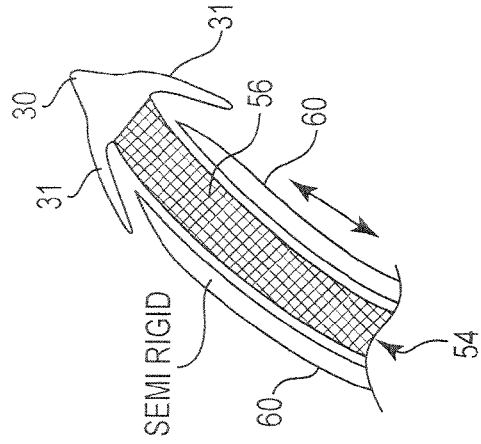
FIG. 16 is a close-up partial cross-sectional schematic view of a slidable tube or sheath, implant and anchor in accordance with embodiments of the present invention.
Figure 17:
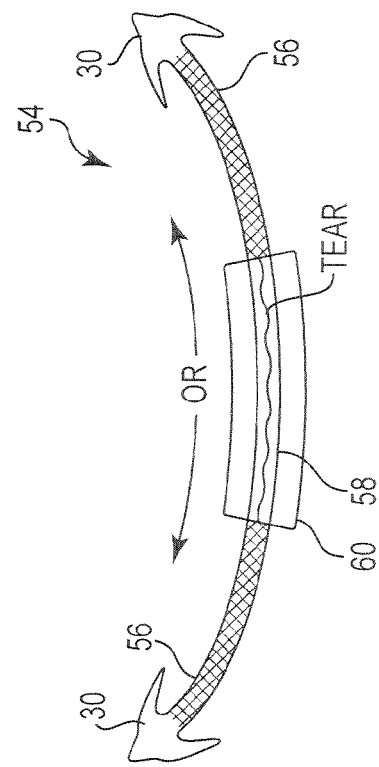
FIG. 17 shows a sling implant system having a slidable or displaceable tube or sheath in accordance with embodiments of the present invention.

Referring to FIGS. 16-17, the tube or sheath 60 can be free floating or adapted to split along a length thereof to facilitate guidance of the needle 16 and moveability of the tube 60. The tube 60 can be constructed of flexible, rigid, or semi-rigid materials known by those of skill in the art. As such, the tube 60 can selectively engage and disengage with the tines 31 of the anchors 30. The moveability of the tube 60 allows it to slide along a length of the sling 54 as shown in FIG. 17, thus facilitating easy removal and optimal positioning during deployment.

Figure 18:
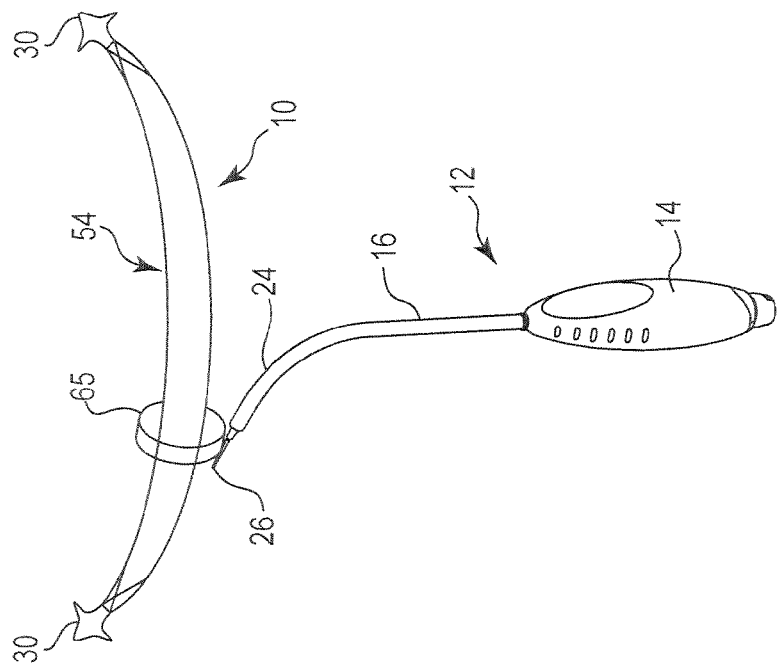
FIG. 18 shows a sling implant system having a sling implant, sliding yoke, and needle delivery device in accordance with embodiments of the present invention.

As shown in FIG. 18, the implant system 10 can include a yoke 65 adapted to slide or move along a length of the implant 54 or sheath 60. Again, the implant 54 can be constructed of mesh, solid material, hollow polymer, and the like. The needle device 12 is adapted to engage the yoke 65 to facilitate attachment with the implant 54 and guidance along the implant 54 and needle 16 during insertion and deployment.

A distal tip 26 of the needle 16 for various embodiments can be elongated to a level that promotes extending out from the lumen in the anchor 30, for holding or securing sutures, and the like. Sutures can be used for docking and alignment of the mesh ends 56 of the implant 54, and can be constructed of a relatively stiff material (e.g., wire, coated suture, semi-rigid polymer, etc.). Parts of the suture may need to remain flexible, portions of the suture can be flexible, while others are rigid or semi-rigid.

Further, the anchors 30 of the implant system 10 can include threading (e.g., female) adapted for twisting/rotating engagement with corresponding threads (e.g., male) in the distal tip 26 of the needle device 12. An actuator, rod, or similar mechanism, in the device 12 can facilitate selective threadable engagement and disengagement of the needle tip 26 with the anchors 30.

The needle device of FIG. 19 can include a distal portion having a bulbous or generally mushroom-shaped element 70 to selectively retain the anchor 30 on the needle tip 26. As such, an actuator 29 in the handle 14 can be activated or engaged to retract or withdraw the element 70 into the needle 16 lumen to release the anchor 30 from the needle tip during deployment. The element 70 can be generally deformable to permit retraction into and extension from the anchor 30 or other device.

As detailed herein, the anchors 30 can include pivotable or otherwise collapsible tines 31. The tines 31 can be in communication with the inner lumen 30a of the anchor 30, such that when the needle tip 26 is inserted into the lumen, the tines 31 pivot or collapse to facilitate insertion of the implant 54. At the point of deployment, the needle and tip 26 is removed, thereby causing the tines 31 to return or spring back to their extended position to facilitate fixation and tissue engagement. Pin, rod, or other flexibility or pivot features can be provided with the anchor tines 31 and anchor 30 in general to facilitate the described and depicted collapsibility and expandability.

The implant systems 10, their various components, structures, features, materials and methods may have a number of suitable configurations as shown and described in the previously-incorporated references. Various methods and tools for introducing, deploying, anchoring and manipulating implants to treat incontinence and prolapse as disclosed in the previously-incorporated references are envisioned for use with the present invention as well. Further, the system and its components or structures can be constructed of known and compatible materials know to those skilled in the art, including metals, polymers, and the like.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

The invention claimed is:

1. A sling implant system for treating a pelvic condition, comprising:
   a sling implant having a support portion and one or more end anchors;
   a needle delivery device having a handle body and a needle, wherein the needle includes a distal end portion adapted for selective engagement with the one or more end anchors of the sling implant;
   an elongate sheath having a proximal end and a distal end, and adapted to at least partially shroud a length of the needle, with the proximal end housed within the handle body; and
   an actuation mechanism having an actuator and at least one cam mechanism housed within the handle body and in operable communication with the elongate sheath, with the actuator including a barrel portion moveable in and out of the handle body such that activation of the actuator operably rotates the sheath about the needle such that the sheath does not move distally, such that the distal end of the elongate sheath rotatably abuts the one or more anchors to deploy the one or more anchors from the distal end portion.

2. The system of claim 1, wherein the one or more end anchors include an end anchor on each end of the sling implant.

3. The system of claim 1, wherein the one or more end anchors include extending anchor tines.

4. The system of claim 3, wherein the elongate sheath includes a barb guard adapted to abut against the extending anchor tines.

5. The system of claim 1, wherein the elongate sheath includes an angled end surface adapted to engage with the one or more anchors such that rotation of the elongate sheath forces the one or more anchors from the distal end portion of the needle.

6. The system of claim 1, wherein the actuator is a pushable button in operable communication with the at least one cam mechanism and rotatable sheath.

7. The system of claim 1, wherein the needle is curved.

8. The system of claim 1, wherein the needle is straight.

9. The system of claim 1, wherein the one or more anchors include at least one internal lumen protrusion and the distal end portion of the needle includes a corresponding mating feature to facilitate snap engagement of the one or more anchors with the distal end portion.

10. The system of claim 9, wherein the at least one internal lumen protrusion includes two opposing internal lumen protrusions.

11. An implant system for treating a pelvic condition, comprising:
    sling implant having a support portion and end tissue anchors;
    a needle delivery device having a handle housing and a needle, wherein the needle includes a distal tip adapted for selective engagement with at least one of the end tissue anchors;
    an elongate sheath having a proximal tip shrouded and rotatable within the handle housing, a distal tip, and adapted to at least partially shroud a length of the needle; and
    an actuation mechanism shrouded within the handle housing and having an actuator in operable communication with the elongate sheath, and including a shaft adapted to traverse in and out of the handle housing, such that activation of the actuator operably rotates the sheath about the needle without moving the sheath distally, such that the distal tip of the elongate sheath rotatably abuts at least one of the end tissue anchors to facilitate deployment.

12. The system of claim 11, wherein the end tissue anchors each include extending anchor tines.

13. The system of claim 12, wherein the elongate sheath includes a barb guard adapted to abut against the extending anchor tines.

14. The system of claim 11, wherein the elongate sheath includes an angled end surface adapted to engage with at least one of the end anchors such that rotation of the elongate sheath forces at least one of the end anchors from the distal tip of the needle.

15. The system of claim 11, wherein the actuator is a pushable button in operable communication with the rotatable sheath.

16. The system of claim 11, wherein the needle is curved.

17. The system of claim 11, wherein the needle is straight.

18. The system of claim 11, wherein at least one of the end anchors includes at least one internal lumen protrusion and the distal tip of the needle includes a corresponding mating feature to facilitate snap engagement of the at least one end anchor with the distal tip.

19. The system of claim 11, further including a second needle delivery device adapted to engage with one of the end anchors.

20. The system of claim 11, wherein the actuation mechanism further includes a cam mechanism adapted to operably facilitate the rotation of the rotatable sheath about the needle.

* * * * *